(12) United States Patent
Champluvier et al.

(10) Patent No.: US 6,939,697 B2
(45) Date of Patent: Sep. 6, 2005

(54) PROCESS TO CONCENTRATE INSOLUBLE PROTEINS BY VIBRATING MEMBRANE FILTRATION

(75) Inventors: Benoit Champluvier, Rixensart (BE); Philippe Jean Gervais Ghislain Permanne, Rixensart (BE)

(73) Assignee: GlaxoSmithKline Biologicals, s.a., Rixensart (BE)

( * ) Notice: Subject to any disclaimer, the term of this patent is extended or adjusted under 35 U.S.C. 154(b) by 0 days.

(21) Appl. No.: 10/250,818

(22) PCT Filed: Jan. 7, 2002

(86) PCT No.: PCT/EP02/00063

§ 371 (c)(1),
(2), (4) Date: Jul. 9, 2003

(87) PCT Pub. No.: WO02/055539

PCT Pub. Date: Jul. 18, 2002

(65) Prior Publication Data

US 2004/0072314 A1 Apr. 15, 2004

(30) Foreign Application Priority Data

Jan. 9, 2001 (GB) .............................................. 0100513

(51) Int. Cl.[7] .............................. C12N 9/00; C07K 1/06
(52) U.S. Cl. ........................................ 435/183; 530/412
(58) Field of Search ................................ 435/183, 69.1, 435/177, 276; 530/412, 376, 377, 414; 426/534, 656, 478, 629; 414/19.7; 210/642, 650

(56) References Cited

U.S. PATENT DOCUMENTS

| 4,872,988 | A |   | 10/1989 | Culkin |              |
|-----------|---|---|---------|--------|--------------|
| 4,900,449 | A | * | 2/1990  | Kraus et al. | 210/651 |
| 5,468,844 | A |   | 11/1995 | Smith  |              |
| 5,911,880 | A |   | 6/1999  | Klein et al. | 210/500.41 |

FOREIGN PATENT DOCUMENTS

EP 0388546 A 9/1990
WO WO 9809717 A 3/1998

OTHER PUBLICATIONS

Exhibit A. avertisment for Pallsap corporation Dynamic membrane and vibrating membrane device.*
Academic Press Dictionary of Science and Technology, Harcourt Press, published at http://www.harcourt.com/dictionary.
Samuel Glasstone, *Textbook of Physical Chemistry*, Macmillan and Co. Ltd., 2nd ed., 1230–1235 (1955).
New Riverside University Dictionary, The Riverside Publishing Company, Houghton Miflin Company, pp. 632 and 1107 (1984).
"Hydrophobic Membranes Keep Water Out While Protecting Components," viewed at Pall Corporation at http://www.pall.com.
Chromatography Filtration (background) posted on QCL-Direct.co.uk, viewed at http://www.qcldirect.co.uk/chromatography/techfiltration2.htm.
Khalil, et al., "on the retentivity of the volatile components of simulated guava juice using ultrafiltration," *Songklanakarin Journal of Science and Techonolgy*, 24, 941–945 (2002).
James S. Johnson, "A New Polyethersulfone Microporous Membrane for Critical Filtrations and Diagnostics," *Business Briefing: Medical Device Manufacturing and Technology*, pp. 1–4 (2002).
Rotating Disk Membrane Filter System, New Membrane–Based Technologies, pp. 763.
Pall Tangential Flow Filtration Membrane, viewed at http://www.pall.com.
Mark Hurwitz, et al., "Shear separation a promising method for protein fractionation retrieved from STN", *Database–Chemical Abstracts Services*, Database Accession No. 133:29905 CA vol. 80(1) pp: 121–127 (2000).

* cited by examiner

*Primary Examiner*—Jon Weber
*Assistant Examiner*—Robert B. Mondesi
(74) *Attorney, Agent, or Firm*—Edward R. Gimmi; Charles M. Kinzig

(57) ABSTRACT

The present invention relates to a process for purifying proteins comprising applying protein extracts to a vibrating membrane fitter equipped with a hydrophilic membrane.

11 Claims, No Drawings

PROCESS TO CONCENTRATE INSOLUBLE PROTEINS BY VIBRATING MEMBRANE FILTRATION

CROSS REFERENCES TO RELATED APPLICATIONS

This application is a National Stage Application filed under 35 U.S.C.§371 of PCT/EP02/00063, filed on Jan. 7, 2002, which claims priority of GB Application No. GB0100513.1, filed Jan. 9, 2001.

The present invention relates to processes for harvesting cell from fermenter broths, the purification of insoluble proteins and the clarification of soluble proteins. In particular the processes utilise vibrating membrane filtration. In particular, the process utilises hydrophilic membranes. Vibrating membrane filters with hydrophilic membrane in particular hydrophilised polyethersulphone membrane are new and form an aspect of the invention.

The production of proteins for diagnostic or biomedical purposes such as for prophylactic and therapeutic applications is achieved economically through cloning and overexpression in host cells such as bacteria, yeasts, insect cells, mammalian cells, and other systems. The cells can be the natural hosts of expression or foreign species allowing easier production conditions.

Some proteins are difficult to isolate in soluble forms even from their natural environment because of their function being structural, or membrane-associated or their location in specific cell compartments. Additionally, the overexpression of proteins in foreign hosts often leads to products being insoluble and accumulating in the form of amorphous deposits or inclusion bodies. The latter are peculiarly well documented using *E. coli* as host for expression (Guise A. D. et al. *Mol Biotechnol* 6, Aug. 1996 (1):53–64).

The causes of protein insolubility in overexpression conditions are not always identified precisely. Insolubility can result from exceedingly high rates of translation, accumulations of high intracellular concentration, unfavorable intracellular environment such as low redox potential and deficiencies in the folding machinery or in the post-translational processing of the host. Association of the proteins with organelles, membranes and other structures of the host cells can result also in insolubility during processing.

Genetic engineering allows the creation of artificial proteins by mutations, deletions or fusions of two unrelated polypeptidic sequences. Often such constructs are insoluble.

Hence, the problem of insolubility in the isolation of proteins is widespread. The insolubility can results from the natural properties of the protein, from the expression in non-natural hosts, or from the deliberate modification of the natural structure by deletion, addition or fusion of polypeptidic elements.

In general, the downstream processing of insoluble proteins involve (1) fractionation of the soluble contaminants away from the product and (2) subsequent solubilisation of the product of interest with buffers at extreme pH or containing solubilising agents such as detergents and chaotropic agents. Guanidine salt and urea are used frequently as chaotropic agents. Inclusion bodies processing methods represent a well know example of methods used for insoluble protein purification.

The classical processes take advantage of the protein insolubility to separate all soluble components of the cells. Protocols for processing insoluble products are described by several papers (Wingfield 1997, Chap. 6 in Current Protocol in Protein Sciences; Misawa S and Kumagai I. *Biopolymers* 1999;51(4):297–307; Mukhopadhyay A. *Adv Biochem Eng Biotechnol* 1997;56:61–109).

The separation can be achieved by several cycles of centrifugation and re-suspension steps allowing to wash out most of the soluble contaminants (Wong H H, O'Neill B K, Middelberg A P. *Bioseparation* 1996;6(6):361–72). Alternatively, the insoluble fraction can be separated from the soluble contaminants using filtration techniques such as depth filtration or tangential flow micro-filtration (Batas B, Schiraldi C, Chaudhuri J B. *J Biotechnol* 1999 Feb. 19;68 (2–3):149–58).

Current techniques suffer from distinct drawbacks. Centrifugation is limited intrinsically by the low size of the insoluble protein fragments and by the viscosity of the medium. Some insoluble protein structures or particulates also show low density differences with the medium. The overall product recovery from repeated centrifugation can be poor for limitations in the technical capability of the machines to separate the pellet from the supernatant. Moreover, scaling up is difficult to predict. Micro-filtration of the extracts containing insoluble proteins and other particulate cell components suffers from membranes plugging and fouling.

After the recovery of the washed insoluble product, the solubilisation of the target protein with detergents or chaotropic agents produces a turbid extract containing particulates, which cannot be applied directly onto chromatography columns without severe plugging. It is thus necessary to clarify such extract by centrifugation and/or micro-filtration. However these techniques suffer from the same shortcoming as indicated above. Additionally even after clarification suspended matter still appears in the extract which thus requires a yet further filtration step prior to any subsequent downstream purification. Moreover, the fouling of micro-filtration membranes often result in poor product transmission into the filtrate.

In attempts to improve the capability of tangential flow micro-filtration, new designs were developed. Kroner and Nissinen (*J. of Membrane Science*, 1998; 36:85–100), Lee et al. (*Biotechnology and Bioengineering*, 1995; 48:386–400), Cole and Brandley (*BioPharm*, 1996; 5:66–71) describe the use of dynamic filtration devices whereby the filter is mechanically driven to produce high shear rates at the membrane surface and thereby better filtration performances in terms of flux, protein transmission and resistance to fouling. However the manufacturing of these types of equipment for large-scale operation has been discontinued.

Alex and Houghney (Chap. 24 in *Filtration in the Biopharmaceutical Industry* 1998, Eds Meltzer T. H. and Jornitz M. W., Marcel Dekker, N.Y.) describe a new device called Vibrating Membrane Filtration allowing to overcome some of the limitations of classical cross-flow micro-filtration. Advantages are presented in terms of better resistance to fouling, improved fluxes and protein transmission. The reference indicates that the membrane material used for most pharmaceutical applications is a microporous PTFE (Teflon) membrane. Examples are given for the recovery of a soluble intracellular product from a cell homogenate. A similar device is described in several publications. U.S. Pat. No. 4,952,317 *Device and Method for Filtering a Colloidal Suspension* describes a vibrating filtration device, likewise U.S. Pat. No. 4,872,988 *Method and Device for Separation of Colloidal Suspensions* describes various vibrating filters peculiarly suited for the clarification of small samples. U.S. Pat. No. 5,014,564 describes the eccentric drive mechanism allowing the operation of a vibrating filtration system.

The present inventors have found that it is possible to purify insoluble protein products by utilising vibrating membrane filters, wherein the filter membrane is hydrophilic such that it can be wetted directly in water. That is the water can penetrate easily the pores of the membranes. Previous vibrating membrane filters have been constructed with hydrophobic material such as PTFE. Such hydrophilic membranes may be produced from regenerated cellulose, cellulose acetate, hydrophilised polymeric material such as PVDF (eg sold under the trade name Durapore by MILLIPORE®, modified nylon, but is preferably a hydrophilised polyethersulphone membrane (hereinafter PES), yet most preferably the hydrophilic membrane "045PS10PES element" purchased from PALL-FILTRON® or its equivalent 0.2 and 0.8 micron membrane.

The invention also provides for a process for purifying an insoluble protein which has the advantages over previous processes in that the filterable contaminants (ie cell debris, nucleic acids, lipids and lipopolysaccaharides) are removed early in the purification process and at a higher efficiency than with previously achievable with prior methods such as with centrifugation, or tangential flow filtration. This enables the product after clarification to be applied directly to a chromatography column. Moreover, the product losses are reduced when compared to tangential flow filtration since such systems are found prone to membrane plugging.

The present invention also has the advantage that the entire process can be maintained as a closed system which greatly facilitates GMP (Good Manufacturing Practices) operations and/or the containment of (bio) hazardous agents. The process is also quicker and less labour intensive. Typically 5 litres of crude extract can be processed in less than 6 hours, usually 3–5 hours. The amplitude of the vibrating membrane filter assembly is set normally between 0.25 and 1.25 inches, typically at about 0.75 inch. The resulting retentate which consists of a suspension of insoluble proteins may be washed, for example by diafiltration, solubilised and filtered through the vibrating membrane filter and the filtrate containing the protein collected, and optionally, applied directly to a chromatography column.

The process of the invention eliminates 80% or more contaminants thereby allowing a relatively pure protein preparation to be purified further by other chromatographic techniques. The invention is also efficient in removing endotoxins from the sample; typically greater than 90% of the endotoxins may be removed from a sample, prior to final purification via a chromatographic column. Suitable chromatographic techniques include IMAC columns, Q-SEPHAROSE® and the like.

Accordingly the present invention provides a process for the purification of protein present in insoluble form comprising applying a cell extract or alternatively a cell homogenate, to a vibrating membrane filter comprising a hydrophilic membrane, preferably PALL-FILTRON® hydrophilic membrane "045PS10PES element" and retaining the protein in the retentate.

The pore size of the membrane are preferably between 0.1 and 1.2 microns. Preferably the pore size is below 0.9 $\mu$m, often about 0.8 $\mu$m, typically about 0.65 $\mu$m more typically between 0.15 $\mu$m and 0.50 $\mu$m. Typically manufacturers' supply membranes with a nominal pore size of 0.2 or 0.45 $\mu$m or 0.8 $\mu$m. These are preferred for use in the present invention.

The starting material, can be any insoluble protein extract from a host cell. For example the following antigens when produced by recombinant expression in insoluble form: tumour rejection antigens such as those for prostrate, breast, colorectal, lung, pancreatic, renal or melanoma cancers. Exemplary antigens include MAGE 1, 3 and MAGE 4 or other MAGE antigens such as disclosed in WO99/40188, PRAME, BAGE, Lage (also known as NY Eos 1) SAGE and HAGE (WO 99/53061) or GAGE (Robbins and Kawakami, 1996, Current Opinions in Immunology 8, pps 628–636; Van den Eynde et al., International Journal of Clinical & Laboratory Research (submitted 1997); Correale et al. (1997), Journal of the National Cancer Institute 89, p293. Indeed these antigens are expressed in a wide range of tumour types such as melanoma, lung carcinoma, sarcoma and bladder carcinoma.

MAGE antigens may be purified according to the present invention and may be expressed as a fusion protein with an expression enhancer or an Immunological fusion partner In one embodiment of the present invention, the derivative is a fusion proteins comprising an antigen from the MAGE protein family linked to a heterologous partner preferably MAGE 3. The proteins may be chemically conjugated, but are preferably expressed as recombinant fusion proteins allowing increased levels to be produced in an expression system as compared to non-fused protein. Thus the fusion partner may assist in providing T helper epitopes (immunological fusion partner), preferably T helper epitopes recognised by humans, or assist in expressing the protein (expression enhancer) at higher yields than the native recombinant protein. Preferably the fusion partner will be both an immunological fusion partner and expression enhancing partner.

The immunological fusion partner may be derived from protein D, a surface protein of the gram-negative bacterium, *Haemophilus influenza* B (WO91/18926). Preferably the protein D derivative comprises approximately the first ⅓ of the protein, in particular approximately the first N-terminal 100–110 amino acids. The protein D derivative may be lipidated. Preferably the first 109 residues of the Lipoprotein D fusion partner is included on the N-terminus to provide the vaccine candidate antigen with additional exogenous T-cell epitopes and increase expression level in *E-coli* (thus acting also as an expression enhancer).

Other fusion partners include the non-structural protein from influenzac virus, NS1. Typically the N terminal 81 amino acids are utilised, although different fragments may be used provided they include T-helper epitopes.

In another embodiment the immunological fusion partner is the protein known as LYTA. Preferably the C terminal portion of the molecule is used. Lyta is derived from Streptococcus pneumoniae which synthesize an N-acetyl-L-alanine amidase, amidase LYTA, (coded by the lytA gene {Gene, 43 (1986) page 265–272} an autolysin that specifically degrades certain bonds in the peptidoglycan backbone. The C-terminal domain of the LYTA protein is responsible for the affinity to the choline or to some choline analogues such as DEAE. This property has been exploited for the development of *E.coli* C-LYTA expressing plasmids useful for expression of fusion proteins. Purification of hybrid proteins containing the C-LYTA fragment at its amino terminus has been described {Biotechnology: 10, (1992) page 795–798}. As used herein a preferred embodiment utilises the repeat portion of the Lyta molecule found in the C terminal end starting at residue 178. A particularly preferred form incorporates residues 188–305.

The immunological fusion partners noted above are also advantageous in aiding expression. In particular, such fusions are expressed at higher yields than native recombinant MAGE proteins. Such constructs are disclosed in Wo99/40188.

Other tumour-specific antigens may be purified according to the invention.

In a further preferred embodiment other antigens are utilised, more partcularly prostate antigens such as Prostate specific antigen (PSA), PAP, PSCA (PNAS 95(4) 1735–1740 1998), PSMA or, in a preferred embodiment an antigen known as Prostase.

Prostase is a prostate-specific serine protease (trypsin-like), 254 amino acid-long, with a conserved serine protease catalytic triad H-D-S and a amino-terminal pre-propeptide sequence, indicating a potential secretory function (P. Nelson, Lu Gan, C. Ferguson, P. Moss, R. Gelinas, L. Hood & K. Wand, "Molecular cloning and characterisation of prostase, an androgen-regulated serine protease with prostate restricted expression, In Proc. Natl. Acad. Sci. USA (1999) 96, 3114–3119). A putative glycosylation site has been described. The predicted structure is very similar to other known serine proteases, showing that the mature polypeptide folds into a single domain. The mature protein is 224 amino acids-long, with one A2 epitope shown to be naturally processed.

Prostase nucleotide sequence and deduced polypeptide sequence and homologs are disclosed in Ferguson, et al. (Proc. Natl. Acad. Sci. USA 1999, 96, 3114–3119) and in International Patent Applications No. WO 98/12302 (and also the corresponding granted patent U.S. Pat. No. 5,955, 306), WO 98/20117 (and also the corresponding granted patents U.S. Pat. No. 5,840,871 and U.S. Pat. No. 5,786, 148)(prostate-specific kallikrein) and WO 00/04149 (P703P).

The present invention provides a process for purifying prostase protein fusions based on prostase protein and fragments and homologues thereof ("derivatives"). Such derivatives are suitable for use in therapeutic vaccine formulations which are suitable for the treatment of a prostate tumours.

In one embodiment the invention contemplates the purification of a mutated prestos antigen wherein the mutation occurs in the active site of the protein. The prestos antigen derivative or fragments and homologues thereof carry a mutation in the active site of the protein, to reduce substantially or preferably eliminate its protease biological activity. Preferred mutations involve replacing the Histidine and Aspartate catalytic residues of the serine protease. In a preferred embodiment, the prestos contains a Histidine-Alanine mutation in the active site, for example at residue 71 of prostase sequence (Ferguson, et al. (Proc. Natl. Acad. Sci. USA 1999, 96, 3114–3119). Corresponding mutation in homologous proteins, for example as disclosed in WO 00/041949 are expressly contemplated. For example this mutation corresponds to position 43 in P703P. This mutation can lead to a significant decrease in the catalytic efficiency (expressed in enzymatic specific activity) of the protein. Preferably the reduction in the catalytic efficiency is at least by a factor of $10^3$, more preferably at least by a factor of $10^6$. The protein which has undergone a histidine alanine mutation is hereafter referred to as * (star).

In one embodiment, the Prostase either mutated or non-mutated is part of a fusion protein, comprising the tumour-associated prostase or fragment or homologues thereof and a heterologous protein or part of a protein acting as a fusion partner. The protein and the fusion partner may be chemically conjugated, but are preferably expressed as recombinant fusion proteins in a heterologous expression system.

In a preferred embodiment the invention contemplated the purification of a prestos fusion protein or fragment or homologues thereof linked to an immunological fusion partner that may assist in providing T helper epitopes. Thus the fusion partner may act through a bystander helper effect linked to secretion of activation signals by a large number of T cells specific to the foreign protein or peptide, thereby enhancing the induction of immunity to the prostase component as compared to the non-fused protein. Preferably the heterologous partner is selected to be recognizable by T cells in a majority of humans.

In another embodiment, the invention provides a process for the purification of a prostase protein or fragment or homologues thereof linked to a fusion partner that acts as an expression enhancer. Thus the fusion partner may assist in aiding in the expression of prostase in a heterologous system, allowing increased levels to be produced in an expression system as compared to the native recombinant protein.

Preferably the fusion partner will be both an immunological fusion partner and an expression enhancer partner. Accordingly, the present invention provides fusion proteins comprising a mutated tumour-specific prostase or a fragment thereof linked to a fusion partner. Preferably the fusion partner is acting both as an immunological fusion partner and as an expression enhancer partner. Accordingly, in a preferred form of the invention, the fusion partner is the non-structural protein from influenzae virus, NS1 (non-structural protein 1) or fragment thereof. Typically the N-terminal 81 amino acids are utilised, although different fragments may be used provided they include T-helper epitopes (C. Hackett, D. Horowitz, M. Wysocka & S. Dillon, 1992, J. Gen. Virology, 73, 1339–1343). When NS1 is the immunological fusion partner it has the additional advantage in that it allows higher expression yields to be achieved. In particular, such fusions are expressed at higher yields than the native recombinant prostase proteins.

In a most preferred embodiment, the fusion protein comprises the N-terminal 81 amino acids of NS1 non-structural protein fused to the 5 to 226 carboxy-terminal amino acids. Alternative expression partners include for example protein D and fragments thereof and C-Lyta as utilised in the context of MAGE antigens.

A further preferred prostate antigen that may be purified is known as P501S, sequence ID no 113 of WO98/37814. Inmmunogenic fragments and portions thereof comprising at least 20, preferably 50, more preferably 100 contiguous amino acids as disclosed in the above referenced patent application. See for example PS108 (WO 98/50567).

Other prostate specific antigens are known from WO 98/37418, and WO/004149. Another is STEAP PNAS 96 14523 14528 7–12 1999.

Other tumour associated antigens useful in the context of the present invention include Plu-1 J Biol. Chem 274 (22)-15633–15645, 1999, HASH-1, HasH-2, Cripto (Salomon et al Bioessays 199, 21–61–70, U.S. Pat. No. 5,654,140) Criptin (U.S. Pat. No. 5,981,215). Additionally, antigens particularly relevant for vaccines in the therapy of cancer also comprise tyrosinase and survivin.

Mucin derived peptides such as Muc1 see for example U.S. Pat. No. 5,744,144, U.S. Pat. No. 5,827,666 WO 8805054, U.S. Pat. No. 4,963,484. Specifically contemplated are Muc 1 derived peptides that comprise at least one repeat unit of the Muc 1 peptide, preferably at least two such repeats and which is recognised by the SM3 antibody (U.S. Pat. No. 6,054,438). Other mucin derived peptides include peptide from Muc 5.

The present invention is also useful for the purification of breast cancer antigens such as her 2/Neu, mammaglobin (U.S. Pat. No. 5,668,267) or those disclosed in WO/00 52165, WO99/33869, WO99/19479, WO 98/45328. Her 2 neu antigens are disclosed inter alia, in U.S. Pat. No. 5,801,005. Preferably the Her 2 neu comprises the entire extracellular domain (comprising approximately amino acid 1–645) or fragments thereof and at least an immunogenic portion of, or the entire intracellular domain approximately (the C terminal 580 amino acids). In particular, the intracellular portion should comprise the phosphorylation domain or fragments thereof. Such constructs are disclosed in WO00/44899. A particularly preferred construct is known as ECD PD a second is known as ECD ΔPD See Wo/00/44899.

The her 2 neu as used herein can be derived from rat, mouse or human.

The Her2-neu antigen may be the entire Her2-neu antigen or portions thereof. Preferred portions comprises the extracellular domain. In a more preferred embodiment there is provided a fusion protein comprising an extracellular domain linked to a portion of the intracellular domain as disclosed in WO 00/44899.

Antigens and proteins from other sources maybe purified according to the process of the invention. Preferably the process of the present invention is utilised to purify an antigen or antigenic composition capable of eliciting an immune response against a human pathogen, which antigen or antigenic composition is derived from the group consisting of antigens of HIV-1, (such as tat, nef, gp120 or gp160). In a preferred embodiment the method of the invention is applied to the purification of an HIV fusion protein known as NEF-TAT and described in WO99/16884. Other antigens include, human herpes viruses antigens, such as gD or derivatives thereof or Immediate Early protein such as ICP27 from HSV1 or HSV2, cytomegalovirus ((esp Human) (such as gB or derivatives thereof), Rotavirus (including live-attenuated viruses), Epstein Barr virus (such as gp350 or derivatives thereof), Varicella Zoster Virus (such as gpI, II and IE63), or from a hepatitis virus such as hepatitis B virus (for example Hepatitis B Surface antigen or a derivative thereof), hepatitis A virus, hepatitis C virus and hepatitis E virus, or from other viral pathogens, such as paramyxovinises: Respiratory Syncytial virus (such as F and G proteins or derivatives thereof), parainfluenza virus, measles virus, mumps virus, human papilloma viruses (for example HPV6, 11, 16, 18, . . . ), flaviviruses (e.g. Yellow Fever Virus, Dengue Virus, Tick-borne encephalitis virus, Japanese Encephalitis Virus) or Influenza virus (whole live or inactivated virus, split influenza virus, grown in eggs or MDCK cells, or whole flu virosomes (as described by R. Gluck, Vaccine, 1992, 10, 915–920) or purified or recombinant proteins thereof, such as HA, NP, NA, or M proteins, or combinations thereof), or derived from bacterial pathogens such as *Neisseria* spp, including *N. gonorrhea* and *N. meningitidis* transferrin-binding proteins, lactoferrin binding proteins, PilC, adhesins); *S. pyogenes* (for example M proteins or fragments thereof, C5A protease, lipoteichoic acids), *S. agalactiae, S. mutans; H. ducreyi; Moraxella* spp., including *M catarrhalis*, also known as *Branhamella catarrhalis* (for example high and low molecular weight adhesins and invasins); *Bordetella* spp., including *B. pertussis* (for example pertactin, pertussis toxin or derivatives thereof, filamenteous hemagglutinin, adenylate cyclase, fimbriae), *B. parapertussis* and *B. bronchiseptica; Mycobacterium* spp., including *M. tuberculosis* (for example ESAT6, Antigen 85 A, -B or -C), *M. bovis, M. leprae, M. avium, M. paratuberculosis, M. smegmatis; Legionella* spp, including *L. pneumophila; Escherichia* spp, including enterotoxic *E. coli* (for example colonization factors, heat-labile toxin or derivatives thereof, heat-stable toxin or derivatives thereof), enterohemorragic *E. coli*, enteropathogenic *E. coli* (for example shiga toxin-like toxin or derivatives thereof); *Vibrio* spp, including *V. cholera* (for example cholera toxin or derivatives thereof); *Shigella* spp, including *S. sonnei, S. dysenteriae, S. flexnerii; Yersinia* spp, including *Y. enterocolitica* (for example a Yop protein), *Y. pestis, Y. pseudotuberculosis; Campylobacter* spp, including *C. jejuni* (for example toxins, adhesins and invasins) and *C. coli; Salmonella* spp, including *S. typhi, S. paratyphi, S. choleraesuis, S. enteritidis; Listeria* spp., including *L. monocytogenes; Helicobacter* spp, including *H. pylori* (for example urease, catalase, vacuolating toxin); *Pseudomonas* spp, including *P. aeruginosa; Staphylococcus* spp., including *S. aureus, S. epidermidis; Enterococcus* spp., including *E. faecalis, E. faecium; Clostridium* spp., including *C. tetani* (for example tetanus toxin and derivative thereof), *C. botulinum* (for example botulinum toxin and derivative thereof), *C. difficile* (for example clostridium toxins A or B and derivatives thereof); *Bacillus* spp., including *B. anthracis* (for example botulinum toxin and derivatives thereof); *Corynebacterium* spp., including *C. diphtheriae* (for example diphtheria toxin and derivatives thereof); *Borrelia* spp., including *B. burgdorferi* (for example OspA, OspC, DbpA, DbpB), *B. garinii* (for example OspA, OspC, DbpA, DbpB), *B. afzelii* (for example OspA, OspC, DbpA, DbpB), *B. andersonii* (for example OspA, OspC, DbpA, DbpB), *B. hermsii; Ehrlichia* spp., including *E. equi* and the agent of the Human Granulocytic Ehrlichiosis; *Rickettsia* spp, including *R. rickettsii; Chlamydia* spp., including *C. trachomatis* (for example MOMP, heparin-binding proteins), *C. pneumoniae* (for example MOMP, heparin-binding proteins), *C. psittaci; Leptospira* spp., including *L. interrogans; Treponema* spp., including *T. pallidum* (for example the rare outer membrane proteins), *T. denticola, T. hyodysenteriae*; or derived from parasites such as *Plasmodium* spp., including *P. falciparum; Toxoplasma* spp., including *T. gondii* (for example SAG2, SAG3, Tg34); *Entamoeba* spp., including *E. histolytica; Babesia* spp., including *B. microti; Trypanosoma* spp., including *T. cruzi; Giardia* spp., including *G. lamblia; Leshmania* spp., including *L. major; Pneumocystis* spp., including *P. carinii; Trichomonas* spp., including *T. vaginalis; Schisostoma* spp., including *S. mansoni*, or derived from yeast such as *Candida* spp., including *C. albicans; Cryptococcus* spp., including *C. neoformans*.

Other preferred specific antigens for *M. tuberculosis* are for example Tb Ra12, Tb H9, Tb Ra35, Tb38-1, Erd 14, DPV, MTI, MSL, mTTC2 and hTCC1 (WO 99/51748). Proteins for *M. tuberculosis* also include fusion proteins and variants thereof where at least two, preferably three polypeptides of *M. tuberculosis* are fused into a larger protein. Preferred fusions include Ra12-TbH9-Ra35, Erd14-DPV-MTI, DPV-MTI-MSL, Erd14-DPV-MTI-MSL-mTCC2, Erd14-DPV-MTI-MSL, DPV-MTI-MSL-mTCC2, TbH9-DPV-MTI (WO 99/51748).

Most preferred antigens for Chlamydia include for example the High Molecular Weight Protein (HWMP) (WO 99/17741), ORF3 (EP 366 412), and putative membrane proteins (Pmps). Other Chlamydia antigens of the vaccine formulation can be selected from the group described in WO 99/28475.

Preferred bacterial antigens derived from *Streptococcus* spp, including *S. pneumoniae* (for example, PsaA, PspA, streptolysin, choline-binding proteins) and the protein antigen Pneumolysin (Biochem Biophys Acta, 1989, 67, 1007;

Rubins et al., Microbial Pathogenesis, 25, 337–342), and mutant detoxified derivatives thereof (WO 90/06951; WO 99/03884). Other preferred bacterial vaccines comprise antigens derived from *Haemophilus* spp., including *H. influenzae* type B, non typeable *H. influenzae*, for example OMP26, high molecular weight adhesins, P5, P6, protein D and lipoprotein D, and fimbrin and fimbrin derived peptides (U.S. Pat. No. 5,843,464) or multiple copy varients or fusion proteins thereof.

Derivatives of Hepatitis B Surface antigen are well known in the art and include, inter alia, those PreS 1, PreS2 S antigens set forth described in European Patent applications EP-A-414 374; EP-A-0304 578, and EP 198–474.

In a preferred embodiment of the present invention the process of the invention may be applied to antigens derived from the Human Papilloma Virus (HPV) considered to be responsible for genital warts (HPV 6 or HPV 11 and others), and the HPV viruses responsible for cervical cancer (HPV16, HPV18 and others). In particular the Early proteins E1, E2 E6 and E7 and fusions thereof.

The most preferred forms of fusion protein are: L2E7 as disclosed in WO 96/26277, and proteinD(⅓)-E7 disclosed in GB 9717953.5 (PCT/EP98/05285).

Particularly preferred HPV 16 antigens comprise the early proteins E6 or E7 in fusion with a protein D carrier to form Protein D-E6 or E7 fusions from HPV 16, or combinations thereof; or combinations of E6 or E7 with L2 (WO 96/26277).

Alternatively the HPV 16 or 18 early proteins E6 and E7, may be presented in a single molecule, preferably a Protein D-E6/E7 fusion.

Other antigens derived from parasites that cause Malaria may be purified according to the process of the invention. For example, preferred antigen from *Plasmodia falciparum* include RTS,S and TRAP. RTS is a hybrid protein comprising substantially all the C-terminal portion of the circumsporozoite (CS) protein of *P.falciparum* linked via four amino acids of the preS2 portion of Hepatitis B surface antigen to the surface (S) antigen of hepatitis B virus. It's full structure is disclosed in the International Patent Application No. PCT/EP92/02591, published under Number WO 93/10152 claiming priority from UK patent application No.9124390.7. When expressed in yeast RTS is produced as a lipoprotein particle, and when it is co-expressed with the S antigen from HBV it produces a mixed particle known as RTS,S. TRAP antigens are described in the International Patent Application No. PCT/GB89/00895, published under WO 90/01496. Other plasmodia antigens that are likely candidates to be components of a multistage Malaria vaccine are *P. falciparum* MSP1, AMA1, MSP3, EBA, GLURP, RAP1, RAP2, Sequestrin, PfEMP1, Pf332, LSA1, LSA3, STARP, SALSA, PfEXP1, Pfs25, Pfs28, PFS27/25, Pfs16, Pfs48/45, Pfs230 and their analogues in Plasmodium spp and may be purified from their insoluble form by the process of the invention.

In a preferred embodiment of the invention the starting material for the invention is a cell extract, such as a cell homogenate from *E. coli* containing one the insoluble proteins: ProtD-Mage3-His, NS1-P703p*-His, ProtD-E7-His, protD-Mage1-His, Naf-TET. Alternatively, the starting material can be a cell homogenate from *Pichia pastoris*, *Saccharomyces cerevisae*, or other expression systems. Alternatively, permeabilized whole cells could be used as well as starting material.

The above proteins can be conveniently produced with an affinity tail such as a poly histidine sequence.

In a preferred embodiment the process of the invention is operated thus:

The vibrating membrane filter e.g. the PallSep VMF is fitted with one or several membranes, for example, up to 100 membranes or more typically 5–50 often between 1 to 20 although 1 to 10 hydrophilic membranes can be utilised. Preferably hydrophulised polyethersulphone membranes are used. Most preferably the hydrophilic membrane "045PS10PES element" purchased from PALL-FILTRON® is used. The membranes utilised will have a pore size ranging between 0.1 microns and 1.2 microns, most preferably between 0.2 and 0.8μ—often between 0.2–0.65 microns. Typically a 0.45 or 0.2 micron membrane is utilised, although in certain embodiments a membrane having a 0.8μ nominal pore size is used.

The VMF unit is operated at a vibration frequency and at amplitude providing the maximum fluxes and transmission through the membrane. Ideally the amplitude of the membrane filter device is between 0.5 and 1 inch, typically about 0.75 inch. The operating conditions are provided by the manufacturer's literature.

Cells are harvested from a fermentation broth and concentrated. In one embodiment, the cells are concentrated and washed using a VMF filter as described herein. Once cells are removed they are homogenised or otherwise extracted. The cell homogenate extraction is circulated on the retentate side of the membrane assembly by means of a pump. The flow rate is in the range of 0.2 to 5 l/min for one square meter of membrane assembly. A gentle pressure is applied to the retentate side of the membrane to force liquid to pass through the filter. To allow for a stable and high transmission of the contaminants the pressure on the retentate side should be less than 25 psi, preferably less than 15 psi and can be less than 10 psi. (Often the pressure is lowest at the beginning of the process and gradually increased). The volume of extract is reduced by the filtration as long as the transmission of the contaminants through the microfilter is significant. The retentate is then washed by diafiltration with an appropriate buffer. This can be made by continuous supply of buffer in the retentate to replenish the volume of liquid eliminated through the filter (continuous diafiltration) or by one or several discrete additions of buffer followed by reduction of volume through the filtration process (discontinuous diafiltration). The volume of buffer for the washing step is selected to maximize the elimination of contaminants through the membrane. Reducing the retentate volume to the desired level can terminate the washing operation.

The product obtained through the above process consists of a suspension of the insoluble protein, which is purified from all soluble impurities and from the fine particles that were able to cross the filter. The buffer composition can be controlled also by the diafiltration procedure.

The present invention allows for greater than $5L/h/m^2$ mean permeation flow rate to be achieved, thus making it very efficient for larger scale procedures, which is approximately double the rate achieved in the same sample with TFF.

Accordingly the present invention provides a process for the purification of an insoluble protein, comprising applying a suspension of the protein to a vibrating membrane filter with a hydrophilic membrane and collecting the insoluble protein in the retentate. This purified extract containing the insoluble product can be processed further in various ways. Usually, one would add a solubilising agent such as guanidine chloride, urea, detergent or a mixture thereof and keep the extract in appropriate conditions of duration, pH and temperature to allow the highest possible dissolution of the protein. The solubilised extract contains particulates, which can be cell wall fragmnents, nucleic acids or other substances.

Because of the particulates, the extract cannot be loaded on chromatography columns without sever plugging. Several options exist to cope with the particulates: fluidized bed or expanded bed adsorption, batch adsorption, centrifugation, filtration or tangential flow filtration. However, the present inventors have found that the vibrating membrane filter used in the conditions detailed above was peculiarly well suited to perform the clarification of the solubilised extract. Filtrate fluxes and product transmissions in the filtrate were higher than with conventional tangential flow filtration.

Accordingly in one aspect of the invention there is provided the use of Vibrating membrane filter, comprising a hydrophilic membrane to clarify a soluble extract of protein.

After clarification, the protein may be further purified, typically by direct application to one or more chromatographic columns, such as immobilised metal ion affinity chromatography, Q-SEPHAROSE® and the like.

The resulting purified proteins can then be formulated with, for example, adjuvants or other pharmaceutically acceptable excipient to produce vaccine or pharmaceutical compositions. Alternatively, the proteins can be utilised as a diagnostic reagent, or for any purpose where purified proteins find utility.

EXAMPLES

General

The combination of steps leading to the production of material purified according to the invention covers the elimination of soluble contaminants through the microfilter, the solubilisation of the desired protein (FIG. 1) and the clarification of the solubilised protein through the microfilter (FIG. 2). This is schematically represented in the flow charts of FIGS. 1 and 2. Additionally the cell harvest can be conducted using the same equipment (see example 8 below).

After clarification, the protein may be further purified, typically by means of one or more chromatographic steps, such as immobilised metal ion affinity chromatography Q-SEPHAROSE® and the like.

The resulting purified proteins can then be formulated with, for example, adjuvants or other pharmaceutically acceptable excipient to produce vaccine or pharmaceutical compositions. Alternatively, the proteins can be utilised as a diagnostic reagent.

Example 1

Purification of ProtD-Mage3-His Protein Expressed in E.Coli as Insoluble Material.

Intracellular overexpression of this fusion protein was obtained in a recombinant E.coli strain as described in WO99/40188. No inclusion bodies were observed under the microscope. Only the first steps of the purification are described (washing of the pellet fraction/solubilization/clarification of the solubilized material). FIG. 3 highlights the main steps and indicate the codes of main samples which are used below in the analyses. The purified extract may then be loaded without any plugging on a chromatographic adsorbent, for example a Sepharose Fast Flow from Amersham Pharmacia.

The details of the experimental procedure were as follows. The cell paste was resuspended at an optical density of 120 (ca. 60 g. dry cell weight per liter) in a pH 7.5, 20 mM phosphate buffer, containing 2 M NaCl and 5 mM EDTA. The cell suspension (5 L) was homogenized by two passes in a Rannie homogenizer at 15000 psi. The cell homogenate represents the extract containing the insoluble protD-Mage3-His. The extract was recirculated at 1 l/min. in the retentate side of the PallSep PS10 equipped with ten 0.45 $\mu$m pore size polyethersulfone (PES) membrane assemblies (0.1 $m^2$ per assembly). The amplitude of the vibration of the membrane assembly was 0.75 inch. The operation was performed at room temperature. The retentate valve was set to produce an overpressure of 2.5 psi on the retentate side and to initiate the filtration of the extract. The volume was reduced from 5 to 2 liters by this filtration. The retentate was washed by diafiltration with 15 liters of diafiltration buffer containing a detergent (20 mM Phosphate buffer pH 7.5-Empigen BB 0.5%) in order to eliminate the maximum amount of contaminants. The filtrate flow-rate was around 10 L/h/$m^2$.

The second phase of the process was initiated immediately with the addition of two liters of solubilization buffer to the retentate (20 mM Phosphate buffer pH 7.5-Empigen BB 0.5%-Guanidine.HCl 8M-Glutathion 20 mM). The solution was recirculated for one hour in the retentate side of the PallSep to allow for the protein to dissolve completely. No filtration occurred during this period.

The recovery of the solubilized protD-Mage3-His was achieved first by filtration with a volume reduction from four to two liters, followed by a diafiltration with six liters of 10 mM Phosphate buffer pH 7.5-Empigen BB 0.5%-Guanidine.HCl 4M-Glutathion 10 mM. The PallSep was operated in the same conditions as for the first filtration. All diafiltrations were made in the continuous mode.

The results obtained in four different experiments are summarized in Table 1 and 2. FIG. 4 shows the SDS-PAGE pattern of samples taken in one of these experiments.

Table 1 indicates the total amount of protein assayed in the main steps of the process. The results are normalized to 100% for the amount of proteins in the cell homogenate (extract). FIG. 4 shows the SDS-PAGE pattern of the fractions obtained during the process. The position of the protD-Mage3-His is indicated by an arrow. The gels contains the samples collected during all steps of the process. The gel on the left shows that a great proportion of contaminants were washed out during the first phase of the process (lane 9 to be compared to lane 2). On the gel on the right side, it appears that after the solubilisation most of the protein of interest was recovered through the membrane in the permeate (lane 7). The pattern of the protein retained on the retentate side of the VMF at the end of the process contained mainly an E. coli protein impurity with little residual protD-Mage3-His (lane 9 on the right gel).

The SDS-PAGE patterns of the samples assayed in Table 1 allows to assign the protein amounts of Table 1 to a great proportion of protD-Mage3-his for the VMF permeate (lane 7 on right gel) and to mainly E. coli contaminants in the VMF wash (lane 9 on left gel).

The main conclusions from these data are as follow. The process allowed to eliminate a major proportion of contaminants in the VMF wash (around 80% of the protein from the extract on average). Further contaminants (around 6% of the protein from the extract) were eliminated in the final clarification in the VMF retentate. Overall, the operations allowed to clean around 86% of the protein contaminants from the extract. Moreover, the major proportion of protD-Mage3-his was recovered in the VMF permeate.

The amount of the LPS (endotoxins) in the processed material is illustrated in Table 2. The amounts of endotoxin found after the VMF operation in four experiments was remarkably low and consistent.

The clearance of endotoxins in the process can be evaluated at about 95% from the comparison of the residual amount measured in the purified ProtD-Mage3-His (ca. 5×10exp9 EU) and the theoretical amount in the cell extract (ca. 10exp11 EU). The total endotoxins in the 5 L of extract was estimated by taking into account the E. coli biomass; the content of 3.4% LPS/dry weight of E. coli cells published by Neidhardt F. C. and Umbarger (Neidhardt F. C. and Umbarger, Chapter 3 in Escherichia coli and Salmonella Cellular and Molecular Biology, $2^{nd}$ Edition, Vol.1, ASM Press, Washington, 1996) and considering an average value of 10 EU/ng LPS.

In summary, the process described allowed to process 5 L of crude E.coli extract to produce a substantially purified preparation containing the major part of the protD-Mage3-His as 8 L of clear solution. All particles from the cell debris were eliminated; as well a majority of the host cell contaminants (86% of the proteins, nucleic acids, circa 99% LPS).

The purification was continued using chromatography techniques of IMAC (Zinc ion chelating Sepharose chromatography followed by Q-Sepharose followed by ultrafiltration. The antigen was formulated with an adjuvant as a vaccine.

This purification sequence was successfully used in the production of material under GMP for clinical supply. The operation described in the invention advantageously replaced the initial process that was based on repeated centrifugation and resuspension to eliminate the soluble contaminants from the product and clarification of the solubilized extract by tangential flow filtration.

The different steps of the process described in the invention took only approximately ½ a working day, (3–5 hours) compared to two working days for the previous process. The process was continuous and required less manpower than the previous one.

Example 2
Purification of NS1-P703P*-His Protein Expressed in E.Coli as Inclusion Bodies Intracellular expression of this fusion protein was obtained in a recombinant E.Coli strain PCT/EP00/06618. In this case, inclusion bodies were clearly observed under the microscope. Only the first steps of the purification are described (washing of the pellet fraction/solubilization/clarification of the solubilized material).

The cell paste was resuspended at an optical density of 120 (ca. 60 g. dry cell weight per liter) in a pH 7.5, 20 mM phosphate buffer, containing 2 M NaCl and 5 mM EDTA. The cell suspension was homogenized by two passes in a Rannie homogenizer at 15000 psi. The cell homogenate represents the extract containing the inclusion bodies. The extract was recirculated at 1 l/min. in the retentate side of the PallSep PS10 equipped with two polyethersulphone (PES) membrane assemblies (0.1 m² per assembly). The amplitude of the vibration of the membrane assembly was 0.75 inch. The operation was performed at room temperature. The retentate valve was set to produce an overpressure of 5 psi on the retentate side and to initiate the filtration of the extract. The volume was reduced from 1 to 0.5 liter by this filtration. The retentate was washed by diafiltration with 3.75 liters of diafiltration buffer (20 mM Phosphate buffer pH 7.5-Empigen BB 0.5%) in order to eliminate the maximum amount of contaminants.

The second phase of the process was initiated immediately with the addition of two liters of solubilization buffer to the retentate (20 mM Phosphate buffer pH 7.5-Empigen BB 0.5%-Guanidine.HCl 8M-Glutathion 40 mM). The solution was recirculated for one hour in the retentate side of the PallSep to allow for the protein to dissolve completely. No filtration occurred during this period.

The recovery of the solubilized NS1-P703P*-His was achieved first by filtration with a volume reduction from one liter to half a liter, followed by a diafiltration with 1.5 liters of 10 mM Phosphate buffer pH 7.5-Empigen BB 0.5%-Guanidine.HCl 4M-Glutathion 10 mM. The PallSep was operated in the same conditions as for the first filtration.

The clarified extract contained the major part of the NS1-P703P*-His from the initial extract, as two liters of clear solution. Thus, the purification sequence used to process the amorphous precipitate of ProtD-Mage3-His of example 1 was shown efficacious also to process a protein expressed as inclusion bodies.

The same advantages as in example 1 were evidenced with this protein: integrated continuous process, short duration, low manpower input, and efficient elimination of contaminants. The clarified extract was purified further by chromatography. This purification sequence was used to produce several clinical batches of purified material which were then formulated with adjuvant to produce a clinical grade vaccine.

Typical results obtained at such scale are summarized in the table 3 below for 3 different experiments:

The protein of interest is nicely detected on gel in this case (major visible band at about 30 Kd) (FIG. 5).

From the $1^{st}$ gel FIG. 5, once again, it is clear that a lot of the contaminants are washed out during the first phase of the process (lanes 3–8 compared to lane 2). After the solubilisation of the washed pellet fraction most of the protein of interest is recovered through the membrane in the permeate upon concentration (lane 9). The recovery of the solubilised material is pursued with the diafiltration (see gel 2, (FIG. 5 bis) lanes 2 to 7). Only a small fraction of the protein is retained on the retentate side of the VMF at the end of the operation. Reducing conditions for the analysis affect the pattern on gel (see gel 2, lanes 6–7 and 8–9).

Example 3
Purification of Nef-Tat-His Protein Expressed in Pichia Pastoris as Insoluble Material Intracellular expression of this fusion protein was obtained in a recombinant Pichia Pastoris strain WO99/16884.

Cell paste was suspended at an OD 100 in 50 mM Phosphate buffer pH 7.5. The cells were broken by four passes in a bead-mill (Dynomill KDL). The extract (10 liters) was processed on the Pallsep PS10 essentially in the same conditions as in example 1, using 10 membrane assemblies. The retentate pressure was around 5 psi. The first volume reduction step was omitted and the continuous diafiltration started from the beginning of the filtration operation. Thirty liters of diafiltration buffer, 10 mM Phosphate buffer pH 7.5-150 mM NaCl, were used.

The Nef-Tat-His was solubilized by addition of 10 liters of 10 mM Phosphate buffer pH 7.5-150 mM NaCl-Guanidine.HCl 8M-Glutathion 80 mM and incubation for 1 hour with recirculation in the retentate side of the system.

The soluble protein was recovered by filtration with an initial volume reduction from 20 to 5 liters, followed by diafiltration with 10 liters of 10 mM Phosphate buffer pH 7.5-NaCl 150 mM-Guanidine.HCl 4M-Glutathion 40 mM.

The clarified, solubilized Nef-Tat-His was recovered in about 25 liters and could be purified further by chromatography.

This purification sequence replaced a previous process whereby several cycles of centrifugation and resuspension steps were used to eliminate soluble contaminants and lipids, followed by solubilization and clarification of the solubilized Nef-Tat by centrifugation and filtration of the supernatant. The same advantages as those listed in examples 1 and 2 were observed. For instance, at a 2L-scale, the VMF process took around 3h30 compared to more than 8h for the prior "centrifugation" process.

The results of the three runs are given on Table 4. The protein of interest is visible on gel at about 35 Kd (major band of the clarified solubilized material lane 4 FIG. 6). During the first phase of the process (washing of the insoluble fraction), a lot of contaminant proteins are washed out (lane 3).

After the solubilsation step, the protein of interest is collected through the membrane in the permeate by concentration and diafiltration (lanes 4–5 and 6). At the end of the VMF operation, only a few contaminant proteins are still detectable in the retentate.

Example 4
Comparison of Performances of the Vibrating Membrane Filter with Non Hydrophilic PTFE Membrane and Hydrophilic PES Membrane for the Purification of Insoluble Proteins
VMF with Non-hydrophilic PTFE Membranes A process similar to what was described in examples 1–3 was assessed to purify the protein HPV18 protD-E7-His WO99/10375 intracellularly produced in E.Coli.

In a first experiment, the PallSep equipped with PTFE 0.45 µm membrane failed to process the protein satisfactorily: despite an acceptable permeation flow rate observed during the washing phase of the insoluble material, the protein of interest was not recovered in the permeate during the solubilization/clarification phase. The results are shown below:

The protein position on gel is indicated by an arrow on FIG. 7 bis.

From gel 1 (FIG. 7) and from gel 2 (lanes 1, 3 and 4), it appears that during the washing phase of the insoluble fraction, some contaminant proteins are washed out.

Nevertheless, from gel 2, lanes 5–8, it appears that very low amount of protein of interest passes through the membrane and is recovered in the VMF-permeate after the solubilisation step. As clearly shown in lane 9, most of the protein of interest stays in the retentate side with a lot of contaminant proteins.
VMF with Hydrophilic Membranes (PES)

However, using hydrophilised polyethersulfone membranes (PES 0.2 µ) as described in the present invention allowed a good recovery of the protein of interest in the filtrate at the end of the whole process.

See SDS-PAGE analysis (Coomassie Blue staining) follow-up of the VMF operation: (FIG. 8 and 8 bis)

The protein position on gel is indicated by an arrow.

Conversely to what was observed with the previous experiment performed on PTFE membrane, most of the protein of interest cross the membrane after the solubilisation step (gel 2, lanes 6–8). No protein of interest is left in the VMF-retentate (gel 2, lane 9).

This comparison stresses the importance of the choice of the membrane to obtain the expected results, whereby hydrophilic membranes like PES were essential compared to the standard PTFE membranes for the PallSep which are hydrophobic.

Example 5
Comparative Evaluation of Non-hydrophilic PTFE Membrane and Hydrophilic PES Membrane for VMF in the Context of the Purification of HPV16 ProtD-E7-His Protein The same comparison as described in example 4 was made in the context of the purification of the protein HPV16 protD-E7-His intracellularly produced in E.Coli (WO 99/10375).

The conclusions were the same: PTFE 0.45 µm membrane did not succeed to process the protein of interest, while PES 0.2 µm membrane did. In particular, the washing step was so efficient to remove very small particles from the extract that the permeate was very turbid. The first run with PES membrane was erroneously aborted by the operator on the basis of the surprisingly high turbidity of the filtrate compared to what was observed with PTFE membranes. The turbidity seemed to indicate that the membrane was damaged, but the analysis a posteriori demonstrated that it was not the case and the insoluble protein of interest was well kept in the retentate during the washing phase.

This observation demonstrated strikingly that the process described in the invention offers unique possibilities to segregate the insoluble protein of interest from very fine particles.

As also described in the previous example, it appears that only a part of the protein of interest cross the PTFE membrane after the solubilisation. Most of the protein is recovered in the VMF-retentate with other contaminating proteins. (See FIG. 9b is lane 14).

On the other hand when the same experiment is performed with PES filters, the protein of interest is easily detectable as the major band in the clarified solubilized fraction, e.g. FIG. 10 bis. (lane 8)

Conversely to what was observed with the previous experiment performed on PTFE membrane, most of the protein of interest cross the membrane after the solubilisation step (FIG. 10 bis, lanes 6–8). Very little protein is left in the VMF-retentate (lane 9).

Example 6
Comparison of the Process Described in the Present Invention with Standard TFF (Tangential Flow Filtration) Technology in the Context of the Purification of the ProtD-Mage1-His Protein The protD-Mage 1-His (WO99/40188) was overexpressed intracellularly as amorphous precipitate in E. coli.

In a first experience, cell extract (OD120) containing the insoluble protein was processed on the PallSep PS10 equipped with two 0.2 µm PES membrane (2×0.1 m$^2$) in conditions very similar to examples 1 and 2.

On the other hand, 1 L of the same extract was treated in the same way on a TFF system with 0.45 micrometer PVDF membrane (MILLIPORE®, 0.5 in$^2$).

The same washing and solubilizing conditions were used to perform the two experiments in parallel.
The results showed:

A better mean permeation flow-rate for the process described in this invention: 7.8 L/h/m$^2$ compared to 4.5 L/h/m$^2$ for the TFF technology.

A better transmission of the solubilized protein of interest during the final clarification step for the process described in this invention, as assessed by SDS-PAGE analysis. Only a fraction of the protein of interest crossed the TFF membrane at that step.

This example demonstrated the superiority of the process described in this invention over the classical TFF technology in terms of yield, purity and filtrate flux.

Several other experiments were performed in the same process conditions but at a 10L-scale and with a PallSep PS10 VMF system equipped with 10 membranes. Mean permeate flow rates for these trials were between 6.8 and 13.2 l/m$^2$h. These were compared with TFF and the results are shown in Table 5 from which it can be concluded that the TFF process, is less efficient in removing contaminants.

The process described in this invention yielded a clarified extract containing less endotoxins with 2.4–21.4 EU/μg protein compared to 3152 EU/μg of protein for the extract obtained by TFF. (Table 6)

Example 7
Comparison of the Process Described in the Present Invention with TFF Technology in the Context of the Purification of the HPV18 ProtD-E7-His Protein As already described above, protein HPV18 protD-E7-His (WO99/10375) was overexpressed intracellularly as amorphous precipitate in E. coli.

In a first experiment, cell extract (OD60) containing the insoluble protein was processed on the PallSep PS10 equipped with two 0.2 μm PES membrane (2×0.1 m$^2$) in conditions similar to previous examples.

As a comparison the cell extract was treated in the same way on different TFF systems:
0.3 micrometer Omega membrane (PALL-FILTRON®), open channel (FIG. 11, 11 bis)
0.2 micrometer PVDF membrane (MILLIPORE®), screen channel ("C") (FIG. 12)
0.2 micrometer PVDF membrane (MILLIPORE®), open channel ("V") (FIG. 13)

The same washing and solubilizing conditions were used to perform the different experiments. The results were analysed by SDS PAGE and are as shown in FIGS. 11, 12 and 13.

From FIG. 11 bis, lane 6 (TFF-permeate, clarified solubilized fraction), it is apparent that very few proteins crossed the 0.3 omega membrane after the solubilisation step, suggesting a clogging of the membrane.

Indeed, all the protein of interest (as shown by an arrow) and other contanminant proteins were recovered in the TFF-retentate fraction at the end of the operation (FIG. 11 bis, lane 7).

In the 0.2 μ PVDF channel C experiment, nearly no protein of interest (arrow) is detected in the TFF-permeate at the end of the whole process (see lane 15, FIG. 12). The transmission of the protein of interest was impaired by the membrane clogging.

The results are only marginally improved with 0.2 PVDF membrane open channel (FIG. 13). Comparing the TFF-retentate fraction at the end of the operation (lane2) FIG. 13 and the TFF-permeate fraction containing the clarified solubilized protein (lane 15), it is clear that only a partial transmission of the protein of interest was obtained after the solubilisation step. So, although open channel was superior to screen channel, the protein transmission was still only partial.

VMF 0.2 Micrometer PES Membrane (PALL-FILTRON®)

In contrast, performing the same operation on the 0.2 PES membrane (see Example 4) the process demonstrated very good transmission of the protein of interest through the membrane after the solubilization step and only minute amount of protein was left in the retentate side at the end of the operation. Table 7 shows the residual endotoxin. The endotoxin was comparable for the three TFF and drastically reduced with the VMF according to the invention.

Example 8
Harvest of E. coli Cells from Fermentation Broth and Subsequent Purification of ProtD-Mage3-His Protein as Insoluble Material.

The fermentation broth can be typically harvested by centrifugation and the cell paste directly (or stored at −20° C. and subsequently) resuspended into the disintegration buffer as described in the example 1.

As described in this example, vibration membrane filtration was used as an alternative method to centrifugation, to concentrate and to wash the E. coli cells present in the fermentation broth. These cells were then removed from the PallSep PS10 equipment and homogenized. This extract was directly reintroduced into the same PallSep PS10 for subsequent purification.

The whole fermentation broth was concentrated up to 3 times, from an optical density of 80 (ca. 40 g. dry weight per litre) to a dry cell weight of ca. 120 g per litre. The whole broth was recirculated at 1L/min in the retentate side of the PallSep PS10 equipped with two 0.45 μm pore size polyethersulfone (PES) membrane assemblies (0.1 m$^2$ per assembly). The amplitude of the vibration of the membrane assembly was 0.75 inch. The operation were performed at room temperature. The retentate valve was set up to produce an overpressure of 5 psi on the retentate side and to initiate the filtration of the whole fermentation broth. The volume was reduced from 3.22 to 1.07 litre by this filtration. The retentate was washed by diafiltration with 3.22 litres of a pH 7.5, 20 mM phosphate buffer containing 2M NaCl and 5 mM EDTA in order to eliminate the maximum of impurities present in the culture medium. This filtrate flow-rate was around 11.5 L/h.m$^2$. Approximately 5% of the total proteins present in the fermentation broth were eliminated during these operations.

The retentate was removed from the filtration system and homogenized directly by two passes in a Rannie homogenizer at 15000 psi. The cell homogenate represents the extract containing the insoluble protD-Mage3-His. The extract was then recirculated at 1 L/min in the retentate side of the same PallSep PS 10 used for harvesting the cells. Between harvest and purification operations, the membrane assemblies and the tubing of the PallSep PS10 were washed first with water and secondly with disintegration buffer in order to eliminate any remaining cell concentrate. The amplitude of the vibration of the membrane assembly was 0.75 inch. The operation was performed at room temperature. The retentate valve was set to produce an overpressure of 5 psi on the retentate side and to initiate the filtration of the extract. The volume was reduced from 0.85 to 0.7 litre by this filtration. The retentate was washed by diafiltration, under an overpressure of 5 to 15 psi, with 5.25 litres of diafiltration buffer containing a detergent (20 mM Phosphate buffer pH 7.5-Empigen BB 0.5%) in order to eliminate the maximum amount of contaminations. The filtrate flow-rate was around 4.2 L/h.m$^2$.

The solubilization phase was then initiated with the addition of 0.7 litre of the solubilization buffer to the retentate (20 mM Phosphate buffer pH 7.5-Empigen BB 0.5%-Guanidine.HCl 8M-Glutathion 20 mM). The solution was recirculated for one hour in the retentate side of the PallSep to allow for the protein to dissolve completely. No filtration occurred during this period.

The recovery of the solubilized protD-Mage3-His was achieved first by filtration with a volume reduction from 1.4 to 0.7 litre, followed by a diafiltration with 2.1 litres of 10 mM Phosphate buffer pH 7.5-Empigen BB 0.5%-Guanidine.HCl 4M-Glutathion 10 mM. The PallSep was operated in the same conditions as for the first filtration. All diafiltrations were made in the continuous mode.

The clarified extract contained the major part of the protD-Mage3-His from the initial extract, as 2.8 litres of clear solution (VMF-permeate). All particles from the cell debris were eliminated; as well as a majority of the host cell contaminants (proteins, nucleic acids, LPS). As shown in the Table below, approximately 60% of total protein present in the whole broth, mostly host cell contaminants were eliminated in the process (VMF-wash), and around 5% of the proteins, mainly cell debris, remained in the VMF retentate.

TABLE

| Phase | Step | Total protein (%) |
|---|---|---|
| Cell harvest | Whole broth | 100 |
| | Washed and concentrated cells | 95.5 |
| Protein purification | Extract | 94.6 |
| | VMF-wash | 60.4 |
| | VMF-retentate | 5.5 |
| | VMF-permeate | 27.3 |

What is claimed is:

1. A process for purifying an insoluble protein comprising applying a suspension of protein to a vibrating membrane filter device comprising a hydrophilic membrane and separating the insoluble protein in a retentate from all soluble impurities and from the fine particles that were able to cross said filter.

2. A process as claimed in claim 1 wherein said membrane has a pore size between 0.1 and 1.2 microns.

3. A process for separating a soluble or solubilised protein extract of protein comprising applying the extract to a vibrating membrane filter comprising a hydrophilic membrane, and collecting the soluble protein in a filtrate.

4. A process of purifying an insoluble protein as claimed in claim 1, comprising the step of solubilising the retentate and re-applying the resulting solubilised protein to the vibrating membrane filter, and collecting the resulting filtrate.

5. A process as claimed in claim 4 wherein said step of solubilising the retentate occurs on the vibrating membrane filter.

6. A process as claimed in claim 1 wherein the hydrophilic membrane is produced from a regenerated cellulose, a hydrophilised polymeric material, a modified nylon or a polyethersulphone membrane.

7. A process as claimed in claim 1 wherein the hydrophilic membrane is a polyethersulphone membrane.

8. A process as claimed in claim 1 wherein a cell expressing said protein in insoluble form harvested from a fermentation broth is concentrated and washed utilising a vibrating membrane filter comprising a hydrophilic membrane.

9. A process for the production of a pharmaceutical composition comprising purifying a protein as claimed in claim 1.

10. A process as claimed in claim 9 wherein the pharmaceutical acceptable excipient is an adjuvant.

11. The process for the production of a pharmaceutical composition of claim 9 wherein comprising in the purifying step subjecting said protein to further downstream chromatographic steps and admixing with a pharmaceutically acceptable excipient.

* * * * *